United States Patent
Stair et al.

(10) Patent No.: US 10,640,435 B2
(45) Date of Patent: May 5, 2020

(54) MULTIMETALLIC CATALYSTS

(71) Applicant: UCHICAGO ARGONNE, LLC, Chicago, IL (US)

(72) Inventors: Peter C. Stair, Northbrook, IL (US); Jeffrey Camacho Bunquin, Westmont, IL (US); Christopher L. Marshall, Naperville, IL (US); Adam S. Hock, Chicago, IL (US)

(73) Assignee: UChicago Argonne, LLC, Chicago, IL (US)

( * ) Notice: Subject to any disclaimer, the term of this patent is extended or adjusted under 35 U.S.C. 154(b) by 332 days.

(21) Appl. No.: 15/157,109

(22) Filed: May 17, 2016

(65) Prior Publication Data
US 2017/0333878 A1 Nov. 23, 2017

(51) Int. Cl.
*B01J 23/00* (2006.01)
*C07C 5/333* (2006.01)
*B01J 23/60* (2006.01)
*B01J 37/02* (2006.01)
*B01J 23/89* (2006.01)

(52) U.S. Cl.
CPC ............ *C07C 5/3337* (2013.01); *B01J 23/60* (2013.01); *B01J 23/8926* (2013.01); *B01J 37/0244* (2013.01); *C07C 2521/08* (2013.01); *C07C 2523/06* (2013.01); *C07C 2523/34* (2013.01); *C07C 2523/42* (2013.01); *C07C 2523/60* (2013.01); *C07C 2523/656* (2013.01); *Y02P 20/52* (2015.11)

(58) Field of Classification Search
CPC .... B01J 23/6562; B01J 23/60; B01J 35/0006; B01J 23/42; B01J 23/34; B01J 23/06; B01J 37/0244; C07C 5/3337; C07C 2523/06; C07C 2523/656; C07C 2523/60; C07C 2523/42; C07C 2523/34; C07C 2521/08
USPC .......................................................... 502/325
See application file for complete search history.

(56) References Cited

U.S. PATENT DOCUMENTS

| 4,005,985 A | 2/1977 | Hutson |
| 4,041,099 A | 8/1977 | Hutson |
| 7,972,569 B2 | 7/2011 | Elam et al. |
| 2014/0094635 A1* | 4/2014 | Lu .................... B01J 21/04 585/658 |

FOREIGN PATENT DOCUMENTS

WO  WO 2012/166514  12/2012

OTHER PUBLICATIONS

Stair et al. "Low-Temperature ABC-Type Atomic Layer Deposition: Synthesis of Highly Uniform Ultrafine Supported Metal Nanoparticles" Angewandte Chemie, vol. 49, Issue 14, Mar. 29, 2010, pp. 2547-2551 (Year: 2010).*
Brookes, New Technology Developments in the Petrochemical Industry, Egypt Petrochemicals Conference, Sep. 27, 2012, 34 pages.
Lu et al., Coking- and Sintering-Resistant Palladium Catalysts Achieved Through Atomic Layer Deposition, Mar. 9, 2012, 35 pages.
UOP LLC, UOP Olefex DeH-16 Catalyst Data Sheet, 2006, 1 page.

* cited by examiner

Primary Examiner — Haytham Soliman
(74) Attorney, Agent, or Firm — Foley & Lardner LLP

(57) ABSTRACT

A multimetallic catalyst having a substrate, intermediate layer and catalyst layer. The catalyst exhibits selectivity greater than 90% and a conversion rate of greater than 30%.

9 Claims, 23 Drawing Sheets

MULTIMETALLIC CATALYSTS

STATEMENT OF GOVERNMENT INTEREST

The United States Government has rights in the invention described herein pursuant to Contract No. DE-AC02-06CH11357 between the United States Department of Energy and UChicago Argonne, LLC, as operator of Argonne National Laboratory.

FIELD OF THE INVENTION

The present invention generally relates catalysts, specifically to multi-metallic catalysts.

BACKGROUND OF THE INVENTION

Catalysts provide a vital mechanism for facilitating modern industrial-scale chemical production. This is particularly true in petrochemical processing and organics. The changing demand for specific hydrocarbon products as well as the changing oil feedstock due to shale oil production competition with traditional crude oil.

Ideally, catalysts facilitate chemical transformations with a certain selectivity for catalyzed reactions (and end products) as well as a stability or useful lifetime as the catalyst is fouled or deactivated. For alkane dehydrogenation, platinum and platinum group materials have long been used as catalysts. However, due to the environment under which the dehydrogenation takes place, platinum catalysts have exhibited a number of problems including poor stability. While high-surface-area substrates have been utilized with platinum catalysts, such as silica and alumina, such catalysts suffer from deactivation due to active-site sintering.

There is a need for a platinum group catalyst that utilizes high-surface area substrates while maintaining catalyst activity, selectivity and stability.

SUMMARY OF THE INVENTION

One embodiment of the invention relates to s catalyst comprising: a substrate; an intermediate layer comprising $MO_x$ where M is a transition metal or main group elemental oxide, the intermediate layer deposited on the substrate; a catalyst layer comprising a platinum group metal, the catalyst layer deposited on the metal oxide intermediate layer.

Another embodiment relates to a catalyst for alkane dehydrogenation comprising: a substrate consisting essentially of silica; an intermediate layer consisting essentially of $MO_x$ where M is a transition metal or main group elemental oxide, the intermediate layer deposited on the substrate; a catalyst layer consisting essentially of a platinum group metal, the catalyst layer deposited on the metal oxide intermediate layer.

Another embodiment relates to a method of forming a catalyst comprising: depositing on a silica substrate by a first method selected from the group consisting of Atomic Layer Deposition (ALD), solution processes (Sol'n) and strong electrostatic adsorption (SEA), an intermediate layer comprising $MO_x$ where M is a transition metal or main group elemental oxide; and depositing on the intermediate layer by a method selected from the group consisting of Atomic Layer Deposition (ALD), solution processes (Sol'n) and strong electrostatic adsorption (SEA), a platinum group catalyst layer.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION OF THE PREFERRED EMBODIMENTS

Figure 1:
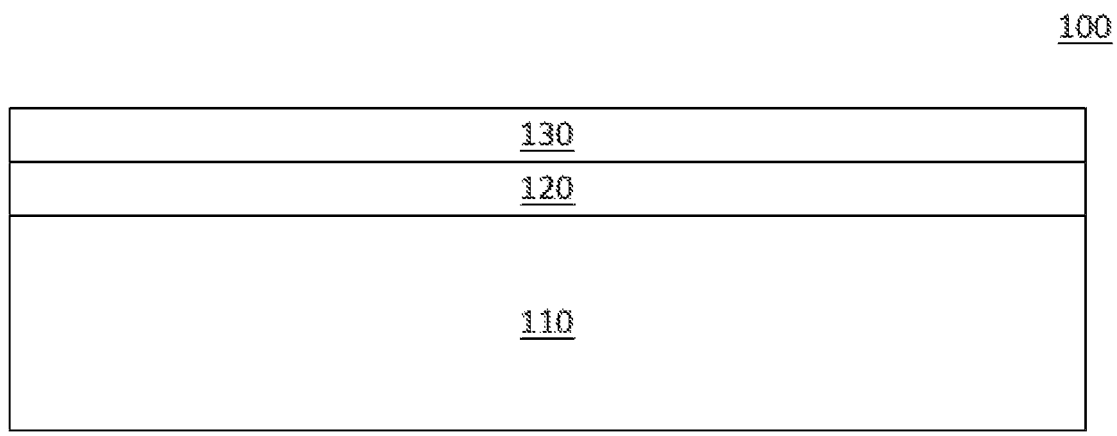
FIG. 1 illustrates an embodiment of a catalyst.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

FIG. 1 illustrates a catalyst 100 having a silica substrate 110, an intermediate layer 120 and a catalytic layer 130. Generally the catalyst 100 comprises $Pt/MO_x/SiO_2$ where the catalyst is a Pt group metal, the intermediate layer 120 is $MO_x$ (M being a transition metal or a main group elemental oxide material) and the substrate layer 110 is $SiO_2$ (silica) and/or $Al_2O_3$ (alumina). The catalyst 100 may facilitate high selectivity and conversion rate for dehydrogenation reactions when compared to known materials utilizing the catalytic layer on a silica substrate or the catalytic layer with other substrates such as alumina. In one embodiment the catalyst 100 is made by thin film deposition techniques, including solution-phase synthesis and gas-phase synthesis, by depositing the intermediate layer 110 on the substrate 100.

The substrate comprises a support material such as silica or alumina. Prior attempts at using silica with platinum as a catalyst has resulted in poor performance including a short life-span due to fouling of the catalyst active sites. See, e.g., U.S. Pat. Nos. 4,005,985 and 4,041,099 describe silica-free dehydration reactors. In one embodiment, the silica substrate is a high surface area substrate and may be formed as a membrane, as a particle (e.g. a bead or powder), or as some other structure. The substrate 100 may be a porous body. In various embodiments the substrate 110 has a surface area, incrementally, of at least 1 $m^2/g$, at least 5 $m^2/g$, at least 10 $m^2/g$, at least 20 $m^2/g$, at least 40 $m^2/g$, at least 60 $m^2/g$, at least 80 $m^2/g$, and/or at least 100 $m^2/g$. In some embodiments, the substrate 100 has a surface area, incrementally, of up to about 10000 $m^2/g$, up to 5000 $m^2/g$, up to 1000 $m^2/g$, up to 500 $m^2/g$, up to 250 $m^2/g$, up to 150 $m^2/g$, up to 120 $m^2/g$, up to 100 $m^2/g$, up to 80 $m^2/g$, and/or up to 60 $m^2/g$. In other embodiments, substrate 100 may have a surface area of more than 10,000 $m^2/g$ or less than 1 $m^2/g$. The supports may be microporous, mesoporous, or macroporous in various embodiments. The particles of alumina/silica may be, in one embodiment, of any size appropriate for the scale of the structure.

In one embodiment the intermediate layer 120 comprises an oxide layer of a transition metal or a main group element. The application of metal oxide promoters improves catalyst stability as evidenced by slower catalyst deactivation. In particular embodiments, the transition metal oxide intermediate layer 120 has the general formal $MO_x$ where M=a transition metal or main group metal, specifically $MO_x$ may include but is not limited to $TiO_2$, $ZrO_2$, $CoO_x$ (x=1-1.5), ZnO, $MnO_x$ (x=1 to 4), $Al_2O_3$, $Ga_2O_3$. Further, the transition metal is, in certain embodiments, a first row transition metal. The intermediate layer 120 has a thickness. In one embodiment the intermediate layer may be such that it does not provide complete coverage of the silica substrate 110. For example, the intermediate layer 120 may be deposited by a thin film deposition technique provide for less than complete loading on the substrate 110 forming a partial mono-layer. In another embodiment a complete monolayer of the intermediate layer 120 is formed. In yet another embodiment the intermediate layer 120 may include at least 2 layers, at least 3 layers, at least 4 layers, at least 5 layers, and/or at least 10 layers.

The catalyst layer 130 includes a catalytic material including, but are not limited to, platinum and platinum group metals. In one embodiment the catalyst layer 130 consists essentially of platinum. In another embodiment, the catalyst layer 130 consists of platinum containing material. The types of Pt and distribution of Pt sites (isolated vs clusters vs particles) vary depending on the synthesis method. It is believed that there is advantage for when the metals are installed by ALD compared to solution-phase synthesis methods. For example, ALD gives more isolated sites than solution-phase synthesis. The catalyst layer 130 may include multiple layers. In some embodiments, the catalyst layer 130 may include at least 2 layers, at least 3 layers, at least 4 layers, at least 5 layers, and/or at least 10 layers.

Each of the substrate 110, intermediate layer 120 and catalyst 130 may be essentially pure such that at least 90% and/or at least 95% of each individual layer is formed from a common type of material.

The catalyst provides a general synthetic approach to silica-based multimetallic catalysts for alkane dehydrogenation with improved stability and selectivity. In one embodiment the general pathway catalyzed by the catalyst 100 is:

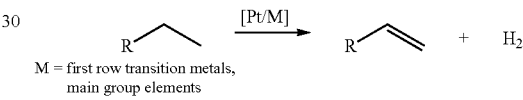

M = first row transition metals, main group elements

Figure 10:
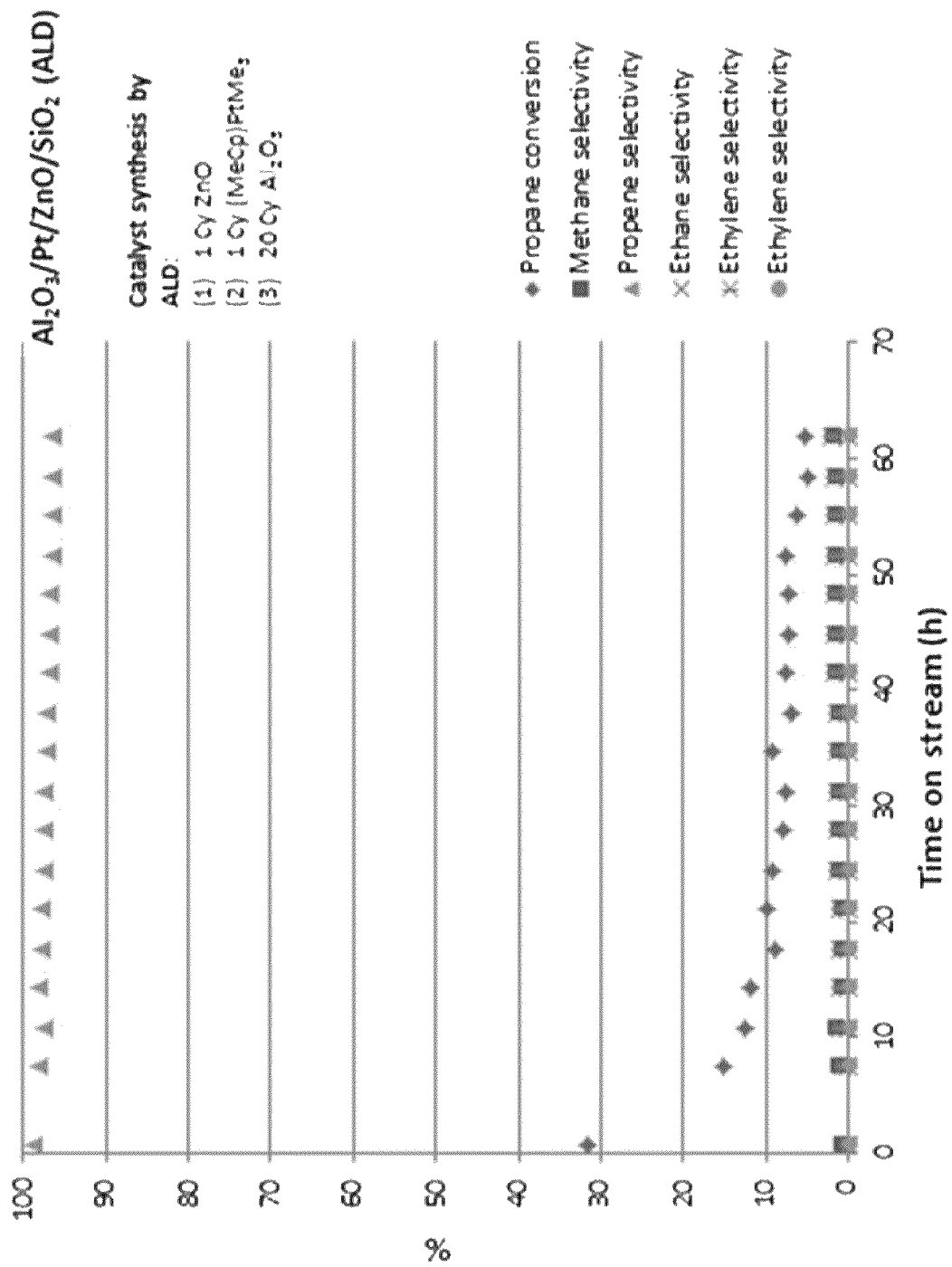
FIG. 10 illustrates conversion and selectivity for $Al_2O_3$/Pt/ZnO/$SiO_2$ (ALD).

In one embodiment the catalyst layer 130 is surface exposed, meaning there is no overcoat deposited on the catalyst layer 130. While the prior art has taught the use of an overcoat, for example of alumina, embodiments using a $Pt/ZnO/SiO_2$ composition have been observed to suffer performance degradation when an alumina overcoat is used. Alumina undercoats are employed to mimic an $Al_2O_3$ surface. FIG. 10 illustrates an embodiment with an undercoat to mimic an $Al_2O_3$ surface as this layer is a more potent support for Pt dehydrogenation catalysts. Alumina overcoats were employed to stabilize Pt sites and prevent them from sintering. Pt sintering causes loss of activity, the results of which can be seen in FIG. 4A.

In addition, while some prior art references have stressed the use of multiple metal oxides as intermediate layers 120, in one embodiment the intermediate layer 120 consists essentially of a single metal oxide, preferably zinc oxide.

Catalysis described herein may be used in a range of temperatures. In one embodiment, the range of temperatures for catalyzing an alkane dehydrogenation reaction is 400° C. to 800° C., 400° C. to 600° C., 400° C. to 500° C., 500° C. to 600° C., 450° C. to 550° C. and 475° C. to 525° C. In one embodiment, a $PT/ZnO$ (10 cycle)/$SiO2$ is stable above 600° C.

Catalysis described herein exhibit a selectivity of at least 80%, at least 90%, at least 92%, at least 94%, at least 95%, at least 96%, at least 98%, at least 99%, or at least 99.5%. In one embodiment the selectivity is for propene, i.e. propane dehydrogenation. In one embodiment, a selectivity of 80 to 90% to propene is observed with a $Pt/MnO_x/SiO_2$ catalyst.

Catalysis exhibit a conversion rate of at least 50%, at least 55%, at least 60%, at least 65%, at least 70%, or at least 75%. In on embodiment the selectivity is for propene, i.e. propane dehydrogenation. In one embodiment the selectivity is observed after at least 10, at least 20, at least 30, at least 40, at least 50, at least 60, or at least 70 hours.

FIG. 1 illustrates an example synthesis method for an embodiment having MOx as the intermediate layer and Pt as the catalyst layer. In general, the intermediate layer is deposited on the silica substrate and the catalyst layer is deposited on the intermediate layer. Experiments have shown that for certain embodiments, ALD synthesis methods give more dispersed ZnO and Pt sites on the oxide surface. More Pt nanoparticles in the precatalyst were observed where both Zn and Pt were installed via solution-phase methods. In one embodiment, the only catalyst that showed stable activity at 600° C. was Pt/ZnO (10 cycles ALD)/SiO2. The high loading of ZnO might be advantageous at higher temperatures.

Figure 2:
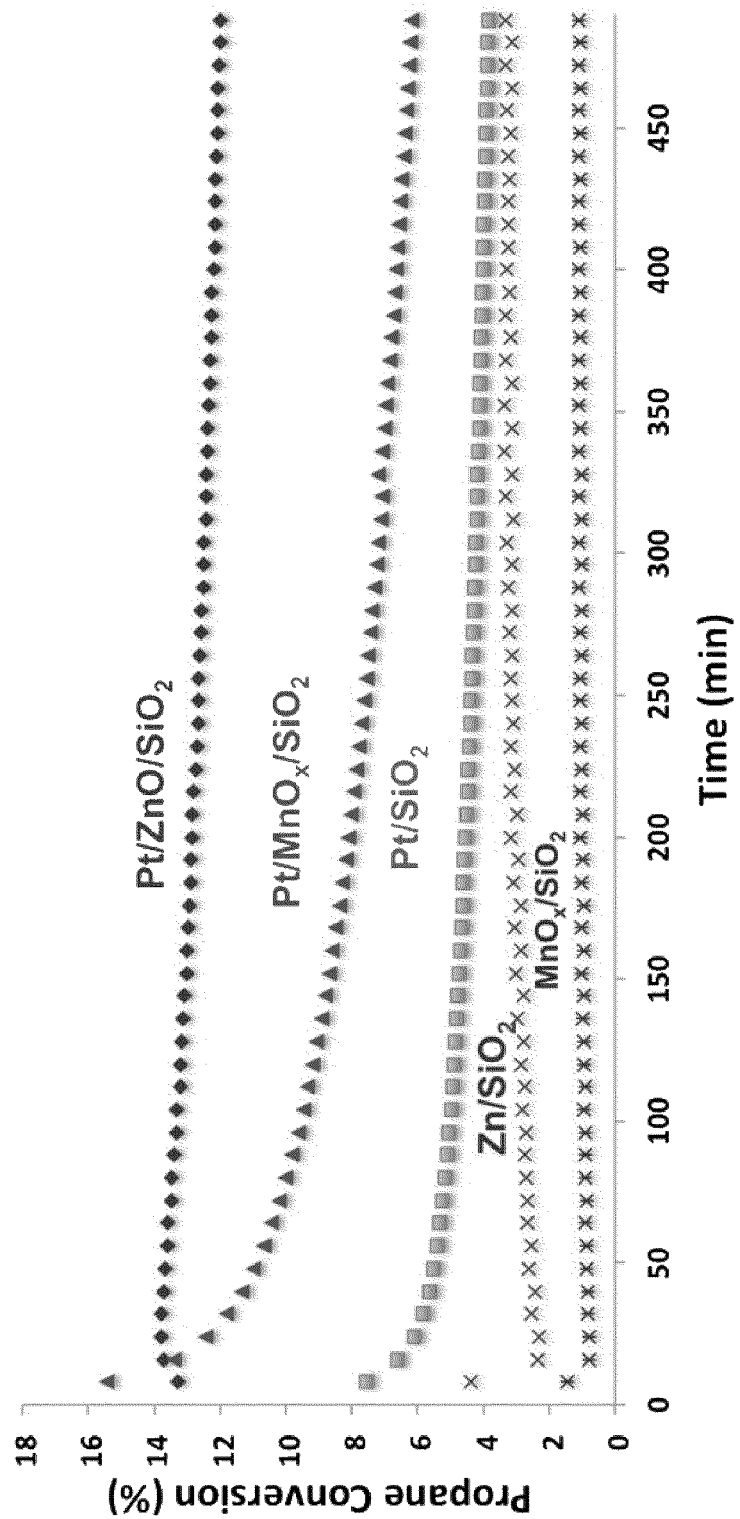
FIG. 2 illustrates Propane conversion for Pt/MOx/SiO2 embodiments as well as known catalyst materials.

FIG. 2 illustrates the results of propane dehydrogenation at 550° C. for two embodiments of the catalyst 100 described herein (Pt/ZnO/SiO2 and Pt/MnOx/SiO2) as well as comparative available catalysts. For this testing plug-flow conditions: 320 mg catalyst, 2.5 mol % $C_3H_8$ (10 sccm), 550° C. The substrate conversion is based on GC analysis of product feed. Pt/$MO_x$/$SiO_2$ Catalysts where M=Zn, Mn; x=1-4 were successfully synthesized via ALD and demonstrated active for propane dehydrogenation.

Figure 3:
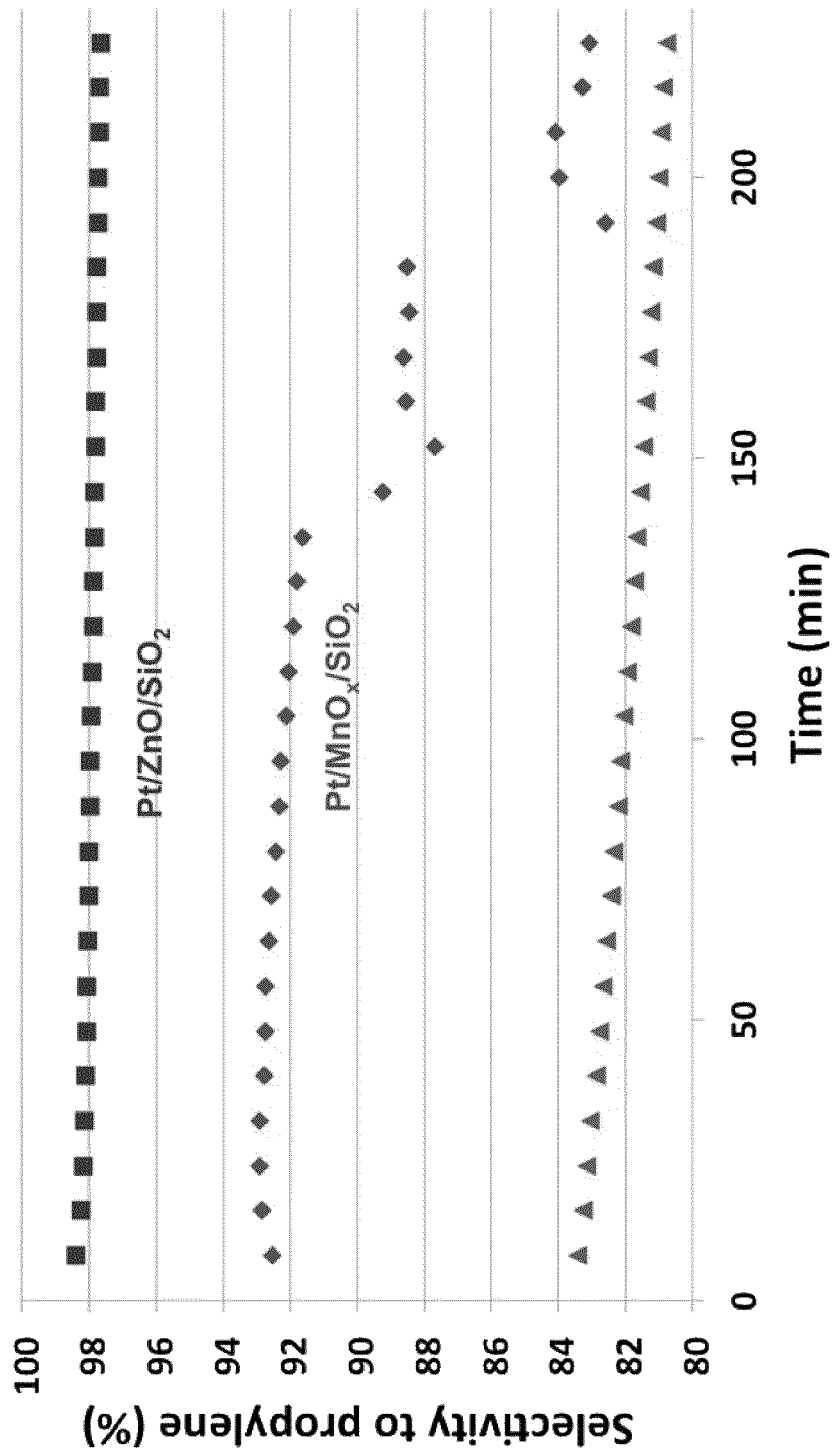
FIG. 3 illustrates a graph of selectivity to propene (also referred to as propylene) over time for two embodiments of a multi-metallic catalyst compared with a platinum on silica catalyst.

FIG. 3 illustrates a graph of selectivity to propene (also referred to as propylene) over time for two embodiments of a multi-metallic catalyst compared with a platinum on silica catalyst.

Figure 4A:
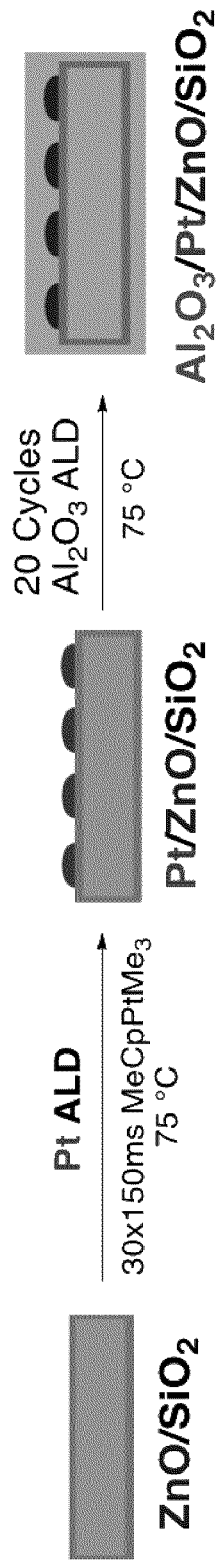
FIG. 4A illustrates a method including the addition of zinc oxide to a silica substrate followed by the deposition of platinum and coating with layers of alumina. The $Al_2O_3$ layers serve as a protective overcoat.
Figure 4B:
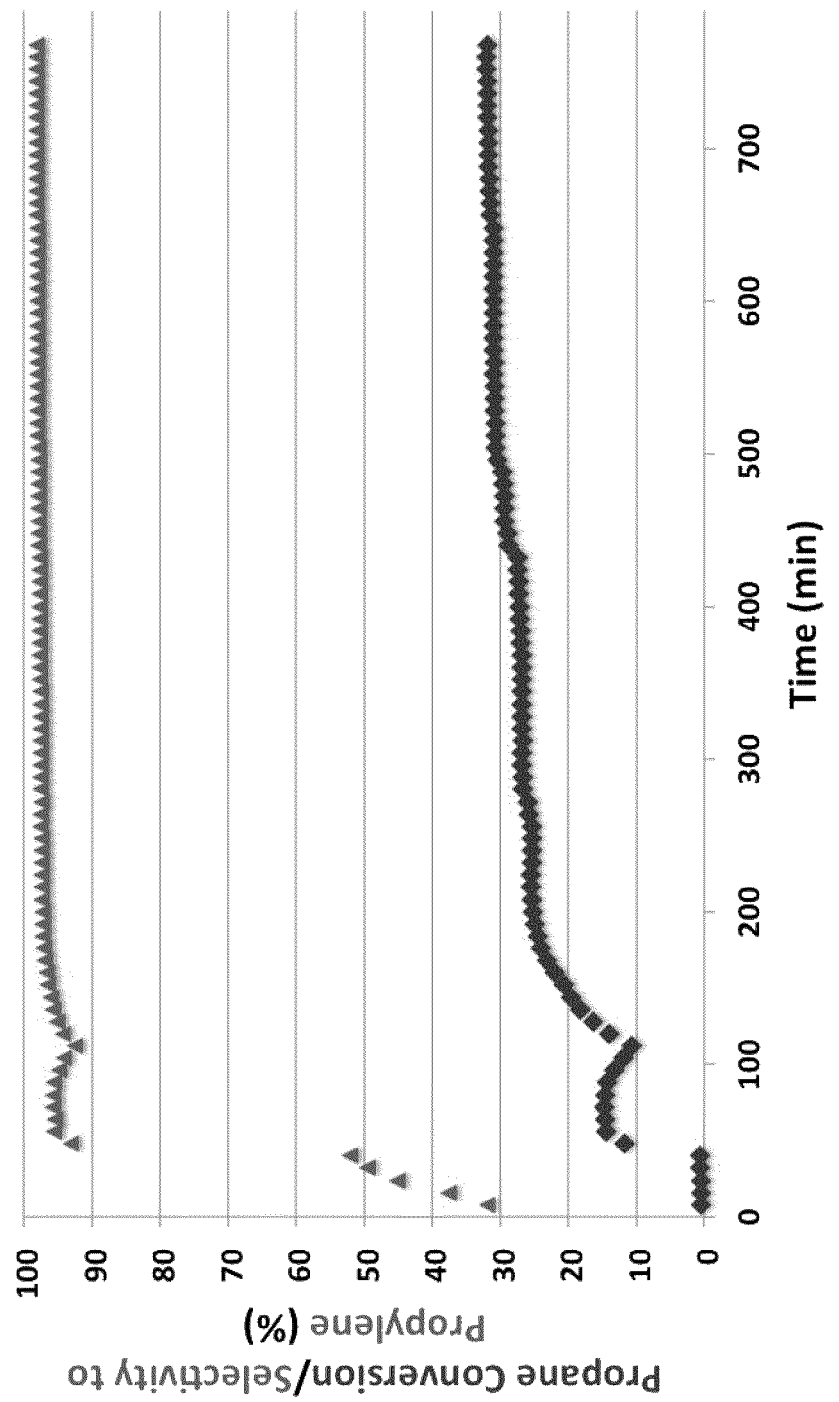
FIG. 4B is a graph of propane conversion and propene selectivity to propene over time for the catalyst of FIG. 4A. The catalyst includes a protective overcoat of $Al_2O_3$.

FIG. 4A illustrates a method including the addition of zinc oxide intermediate layer 120 to a silica substrate 110 followed by the deposition of platinum as a catalyst layer 130 and coating with overcoat layers 140 of alumina. FIG. 4B is a graph of propane converts and propene selectivity to propene over time for the catalyst of FIG. 4A.

Figure 5:
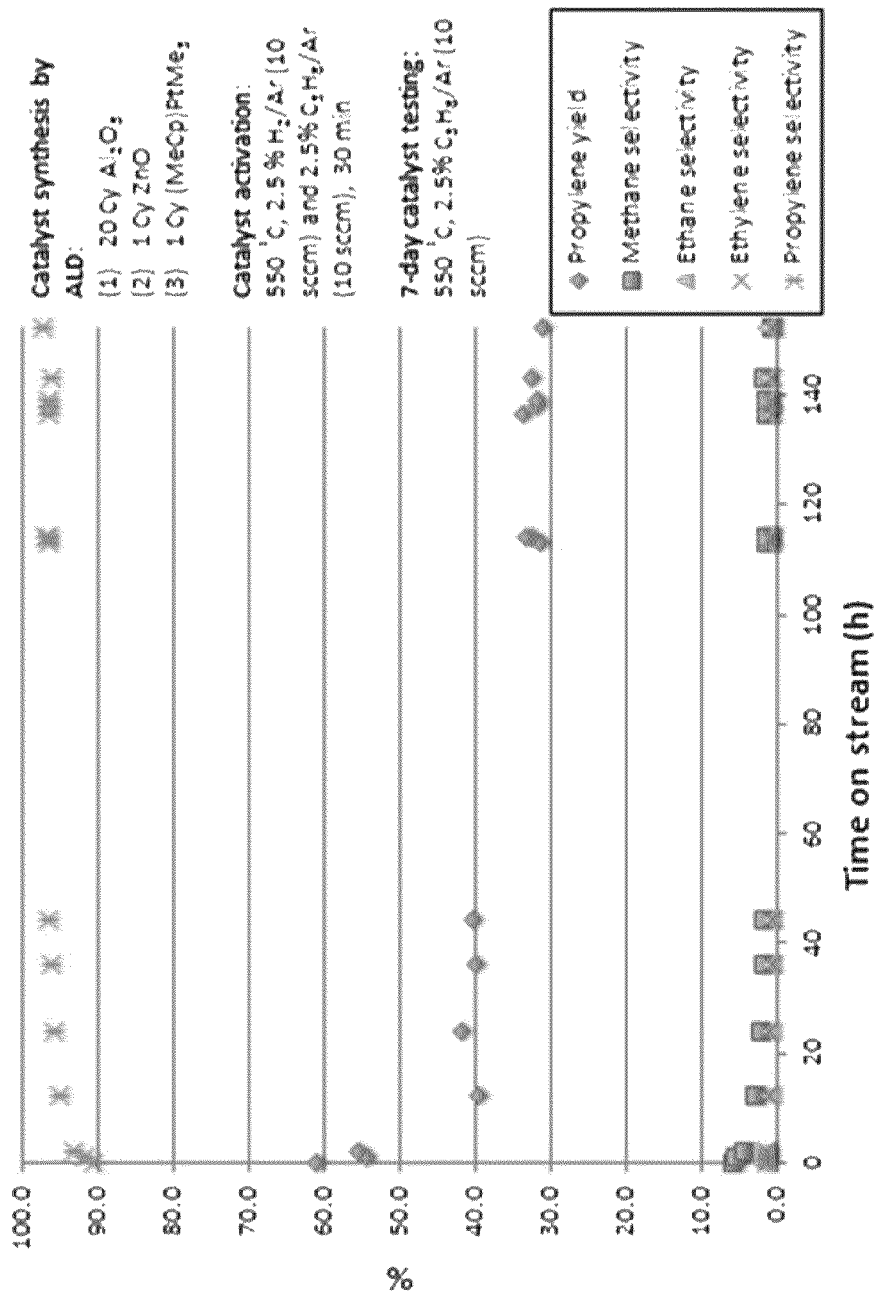
FIG. 5 is a graph of catalyst properties for one embodiment through a 6.5 day test run.

FIG. 5 is a graph of catalyst properties for one embodiment through a 6.5 day test run. The catalyst used to generate the data in FIG. 5 was synthesized on a silica high surface area substrate by ALD using 20 cycles of alumina deposition, one cycle of zinc oxide and one cycle of platinum deposition ((MeCP)PtMe$_3$). For the example of FIG. 5, the order of deposition was: (1) $Al_2O_3$, (2) ZnO, and (3) Pt. Catalyst activation was at 550° C. by 2.5% H2/Ar (10 sccm) and 2.5% C3H8/Ar (10 sccm) for 30 minutes and testing was then carried out at 550° C. with 2.5% C3H8/Ar (10 sccm). As can be seen, propene yield and selectivity remained high throughout the test with selectivity slightly increasing after an initial catalyst activation and propane conversion slightly decreasing.

Figure 6:
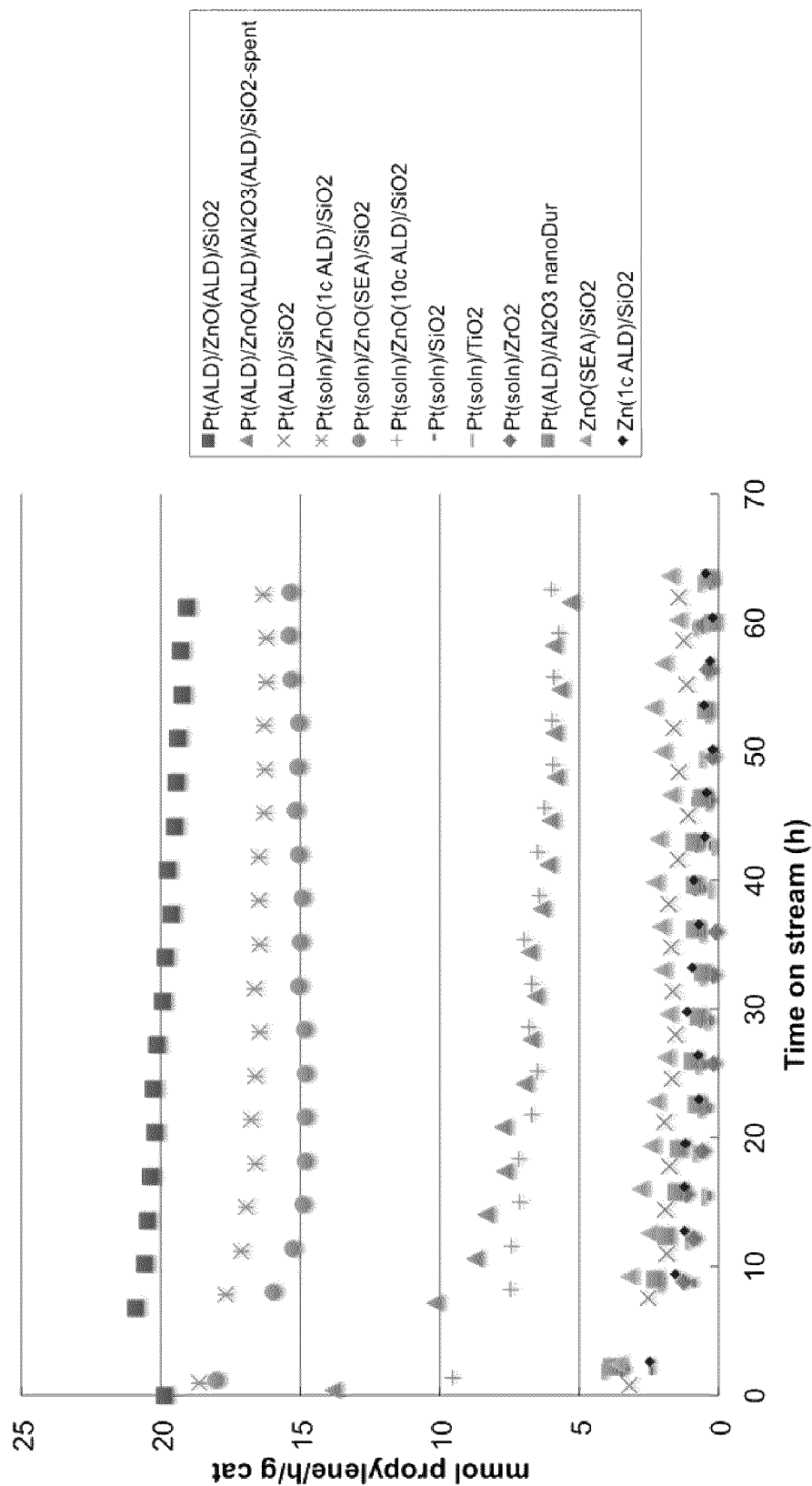
FIG. 6 illustrates a comparison of embodiments described herein as well as versus other catalysts.

FIG. 6 illustrates a comparison of embodiments described herein as well as other catalysts. Catalyst activation was at 550° C. by 5% H2/Ar (5 sccm), pure H2 (2 sccm) and He (2 sccm) for 30 minutes and testing was then carried out at 550° C. with 5% H2/Ar (5 sccm), He (2 sccm). Controls of just supports silica and alumina show negligible propane conversion. Platinum systems having a zinc oxide layer on the silica substrate exhibited the highest conversion rate and a steady rate through the testing.

Various synthesis methods may be used for depositing the platinum group metal, the transition metal and the silica. For example, synthesis methods may include thin-film deposition techniques, such as but not limited to Atomic Layer Deposition (ALD), solution processes (Sol'n) or strong electrostatic adsorption (SEA). In many exemplary embodiments, one or more of the catalyst layer 130, the intermediate layer 120 and the substrate 110 can be form by atomic layer deposition (ALD). ALD utilizes alternating exposures between precursors (e.g. in a gaseous form) and a solid surface to deposit materials in a monolayer-by-monolayer fashion. This process can provide uniformity of the coatings in many embodiments, including on nanoporous substrate materials. In many embodiments, this process also allows good control over the thickness and composition of the coatings. FIG. 6 shows that the three highest performing catalysts each comprises Pt/ZnO/SiO2, just utilizing different synthesis to create the catalyst. One sample utilized ALD for deposition of both the Pt and ZnO, another sample utilized ALD for ZnO but used a solution phase process for deposition of the platinum and a third sample used SEA for ZnO and solution-phase for platinum. The types of Pt and distribution of Pt sites (isolated vs clusters vs particles) vary depending on the synthesis method. It is believed that there is an advantage for when the metals are installed by ALD compared to solution-phase synthesis methods.

Figure 14:
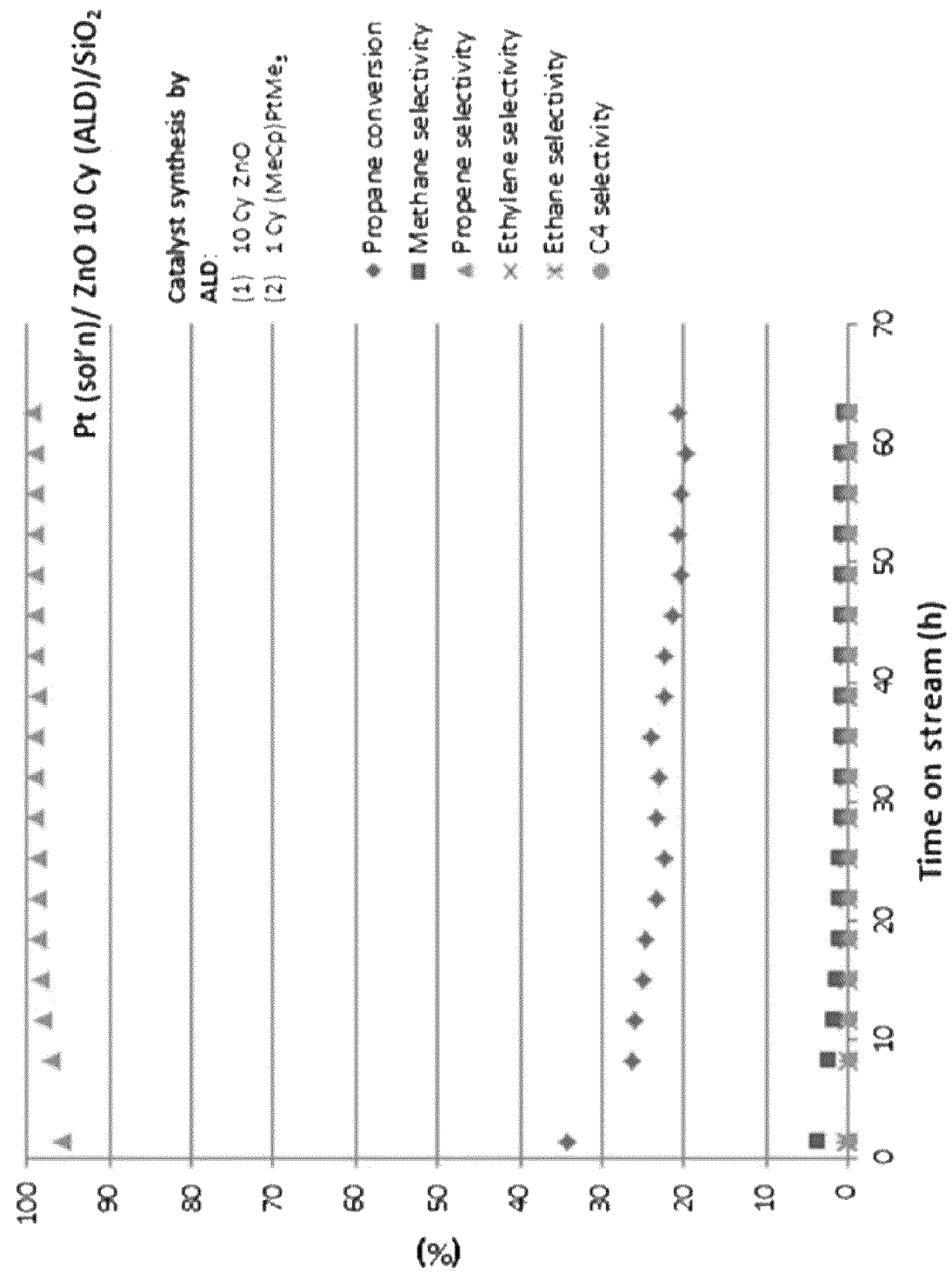
FIG. 14 illustrates conversion and selectivity for Pt(Sol'n)/ZnO(10Cy-ALD)/$SiO_2$.
Figure 15:
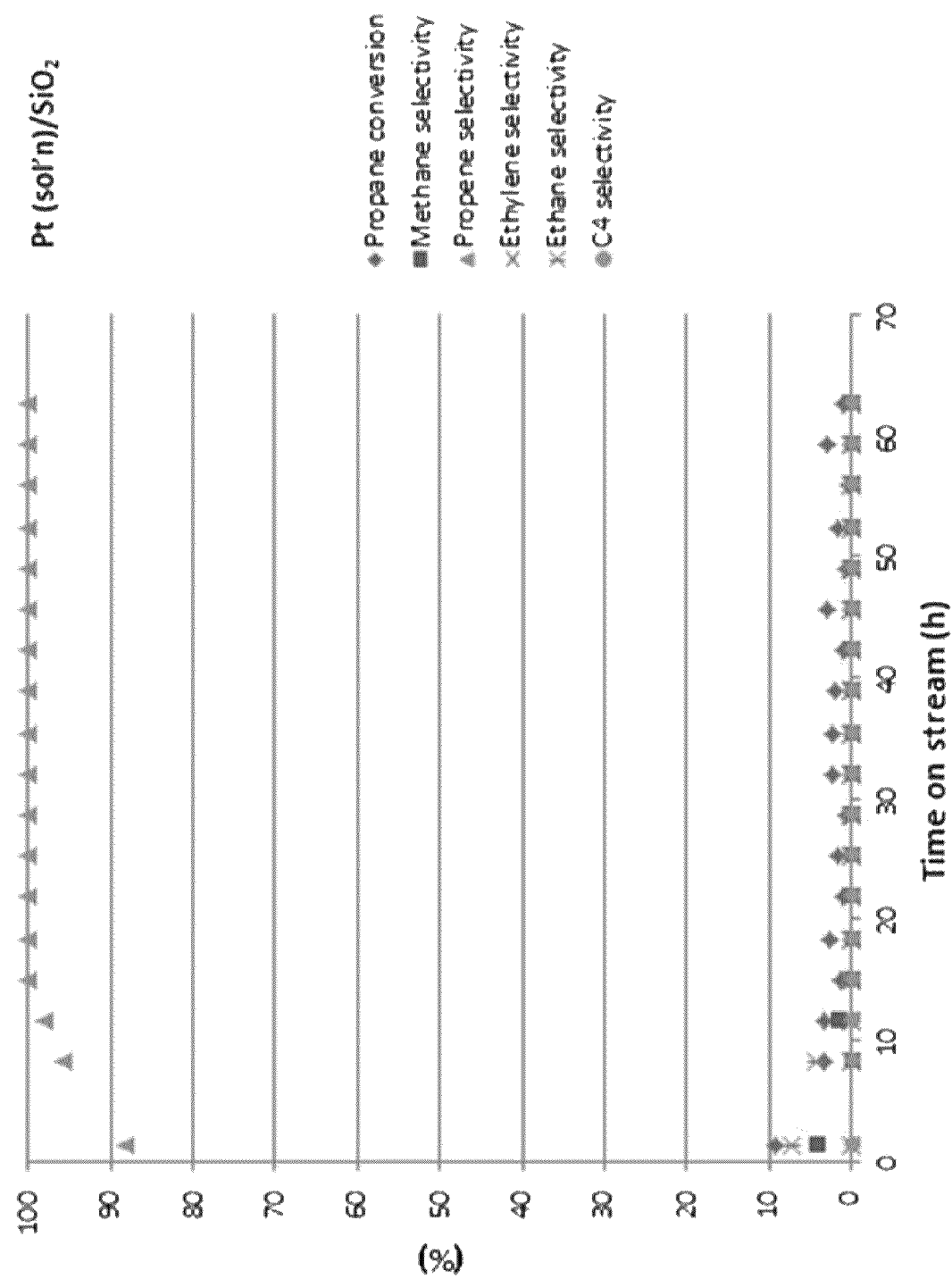
FIG. 15 illustrates conversion and selectivity for Pt(Sol'n)/$SiO_2$.

Variations with either a thick (10 cy vs 1 cy) zinc layer or an alumina layer under the platinum in addition to the zinc oxide also showed notable conversion rates above the controls but well below the Pt/ZnO/SiO2 embodiments. Variations among the amount of zinc loading illustrate that silica surface saturation with ZnO, that is a monolayer, gives the highest catalytic activity. The alumina overcoat reduces the number of exposed sites, hence the lower conversion rates observed. Further, the overcoat increases stability (slower deactivation rate) of the catalyst by preventing active site sintering. FIG. 14 further confirms that thicker (here 10 cycles of ALD) transition metal layers result in a reduction in propane conversion.

Figure 7:
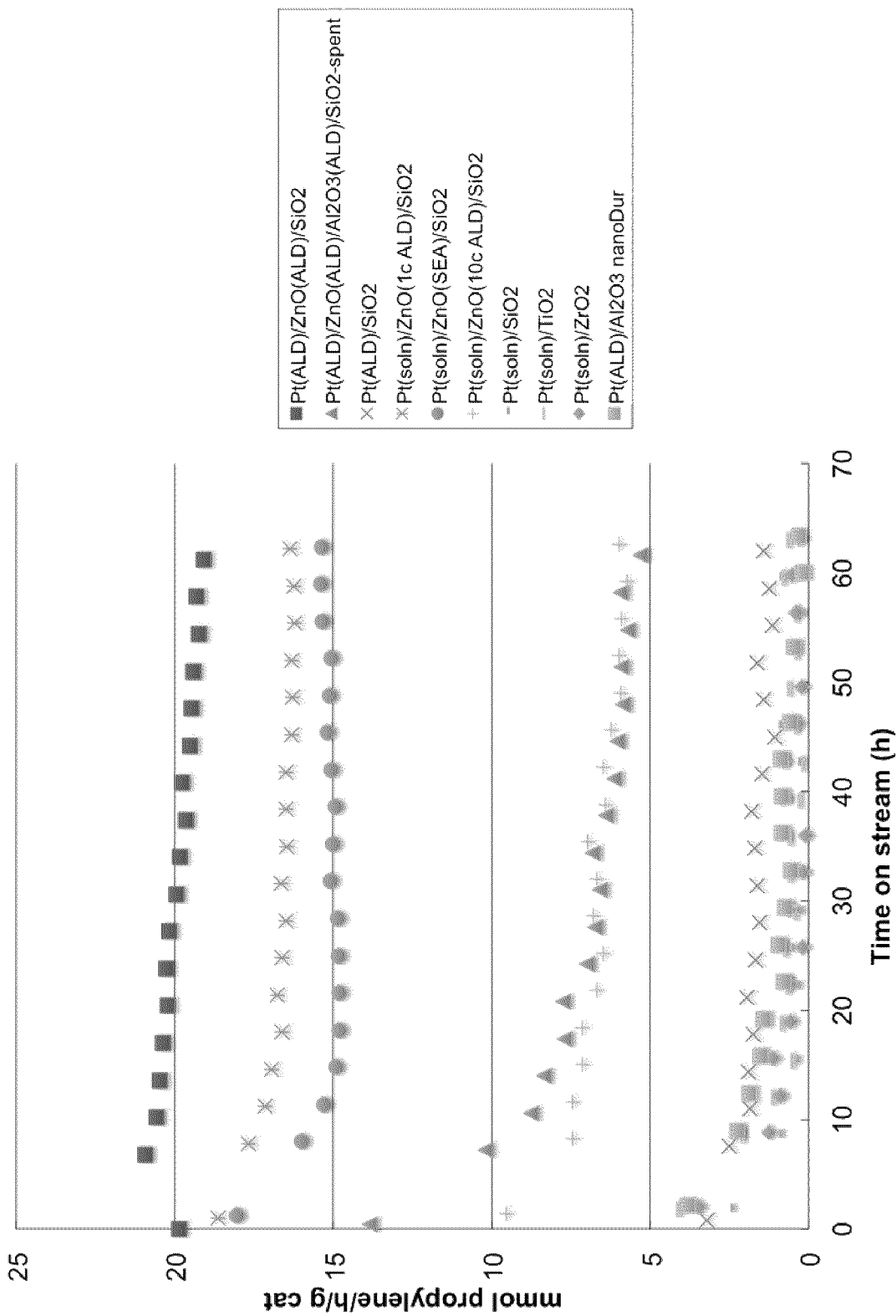
FIG. 7 provides a performance summary of a number of Pt-based catalysts in comparison to embodiments of a catalyst with a metal oxide coating over a silica substrate.

FIG. 7 provides a performance summary of a number of commercial Pt-based catalysts in comparison to embodiments of a catalyst with a metal oxide coating over a silica substrate. Performance is reported in terms of turn-over frequency of the catalyst as a function of time. As with the conversion rate in FIG. 6, the best performance was again observed in Pt/ZnO/SiO2. The embodiments synthesized by ALD showed the highest performance, along with related embodiments using different synthesis techniques Pt(sol'n)/ZnO(ALD)/SiO2 and Pt(Sol'n)/ZnO(SEA)/SiO2. As was seen with propane conversion, the Pt/ZnO/SiO2 catalysts show a marked improvement over the prior art catalysts.

Figure 12:
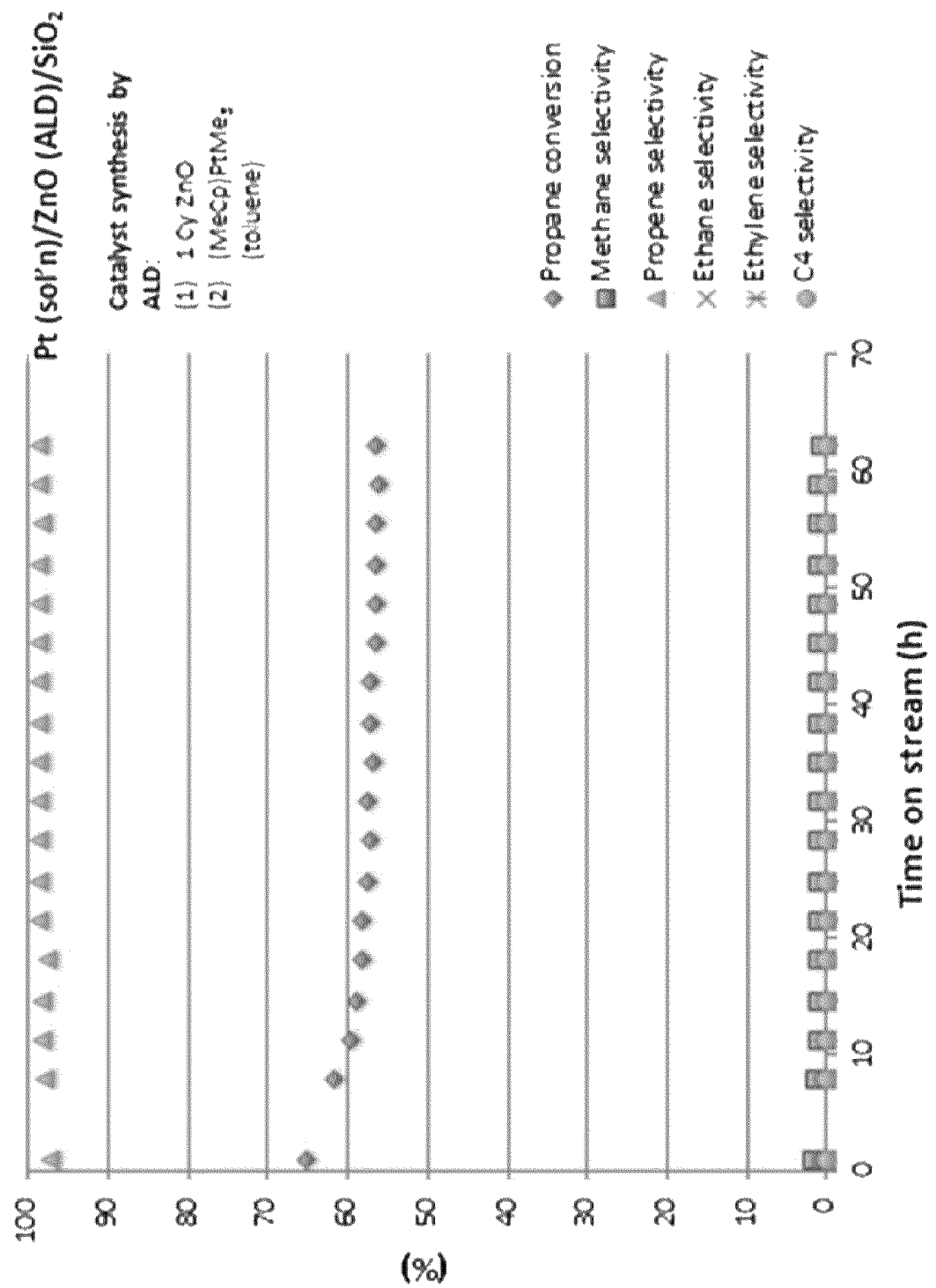
FIG. 12 illustrates conversion and selectivity for Pt(Sol'n)/ZnO(ALD)/$SiO_2$.
Figure 13:
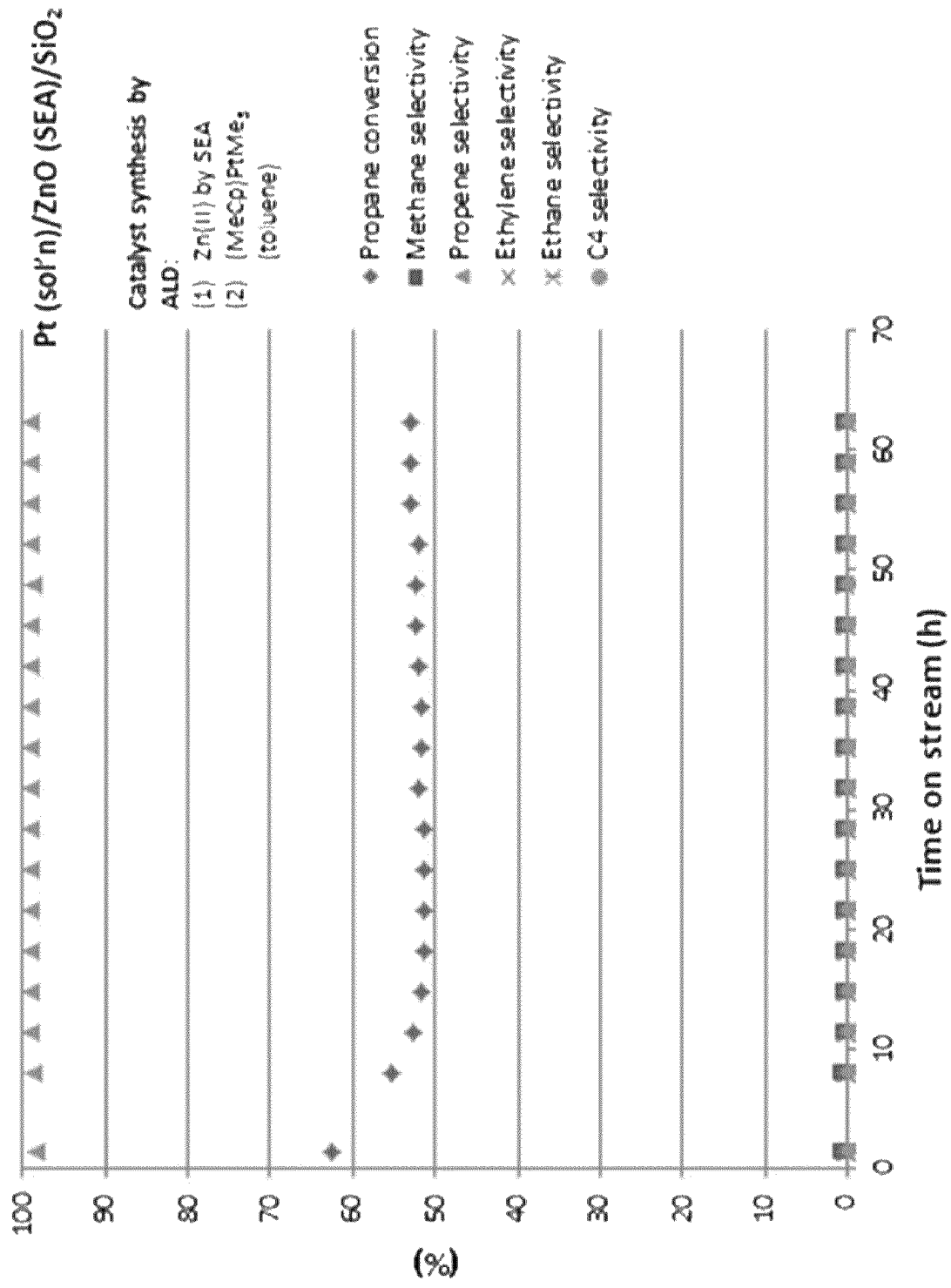
FIG. 13 illustrates conversion and selectivity for Pt(Sol'n)/ZnO(SEA)/$SiO_2$.

FIGS. 8-22 illustrate conversion and selectivity data for certain embodiments described herein as well as for commercial catalysts and control materials. Consistent with the observations previously noted, propane conversion and propene selectivity are both seem as surprisingly and critically improved over both the controls (such as the bare substrates) as well as commercial catalysts. The Pt/ZnO/SiO2 embodiments demonstrate both markedly high conversion rates, ~70% as well as selectivity approaching 100%. The embodiments synthesized by ALD (FIG. 8) showed the highest performance, along with related embodiments using different synthesis techniques Pt(sol'n)/ZnO(ALD)/SiO2 (FIG. 12) and Pt(Sol'n)/ZnO(SEA)/SiO2 (FIG. 13).

Figure 16:
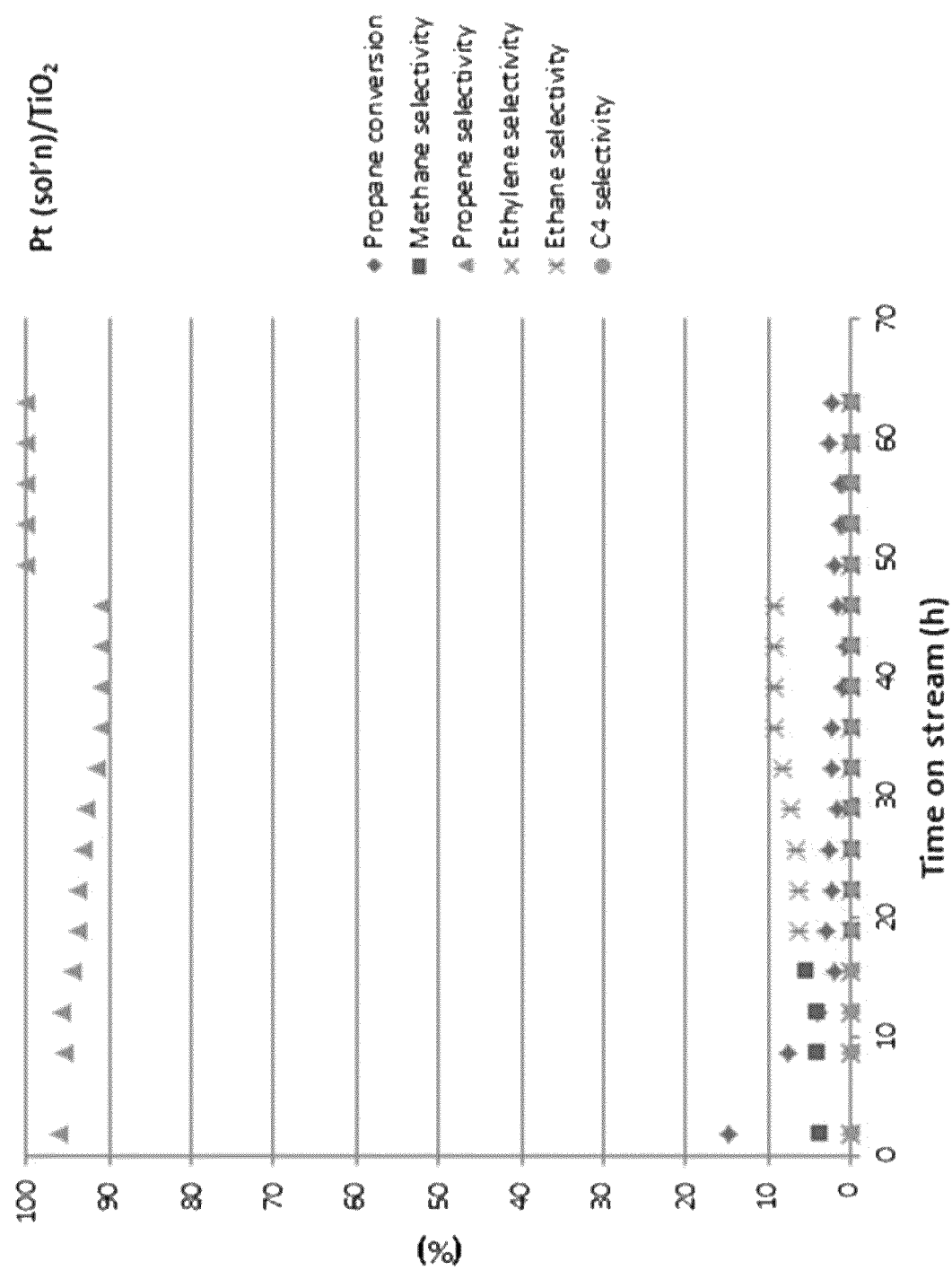
FIG. 16 illustrates conversion and selectivity for Pt(Sol'n)/$TiO_2$.
Figure 17:
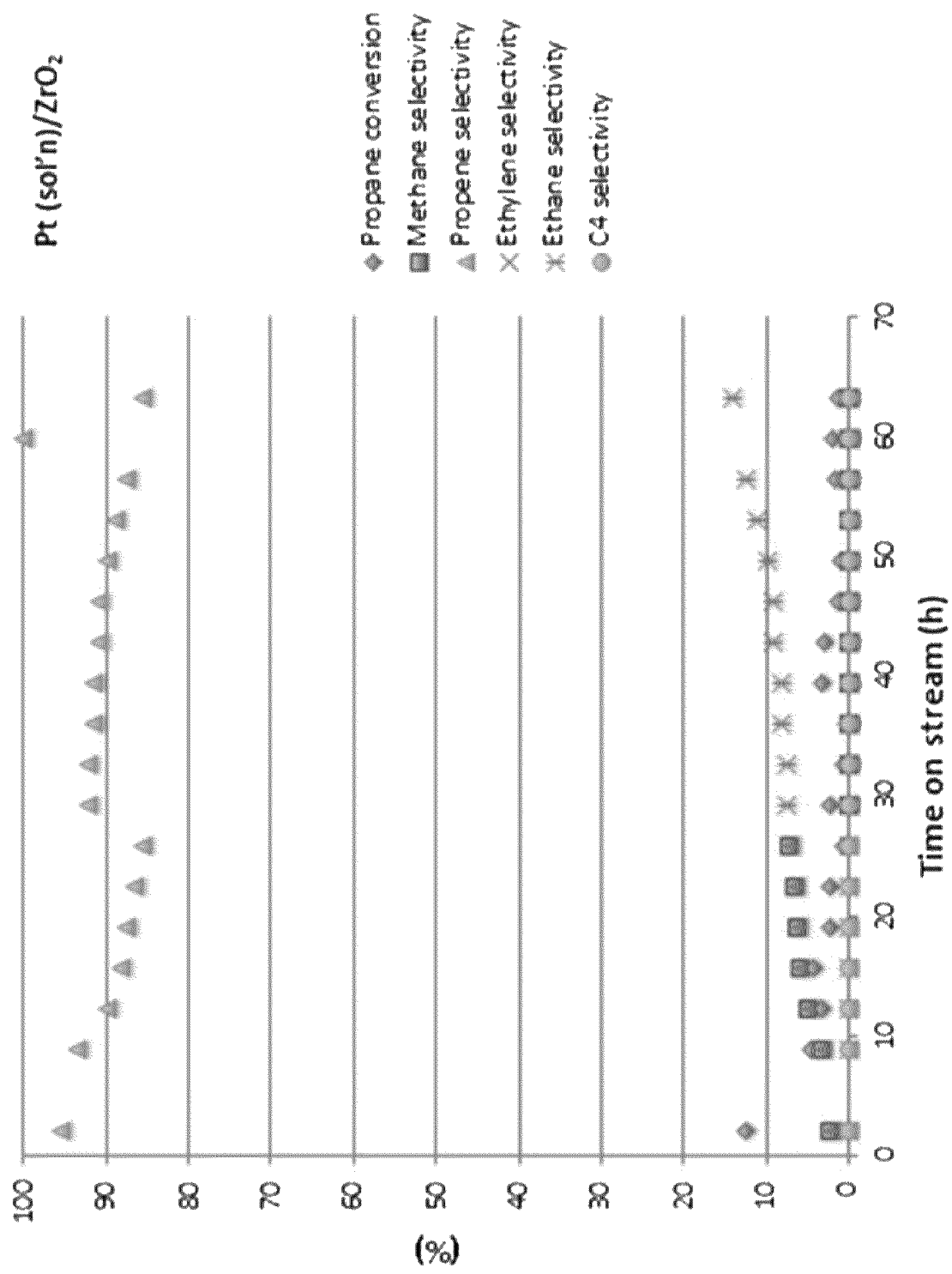
FIG. 17 illustrates conversion and selectivity for Pt(Sol'n)/$ZrO_2$.
Figure 18:
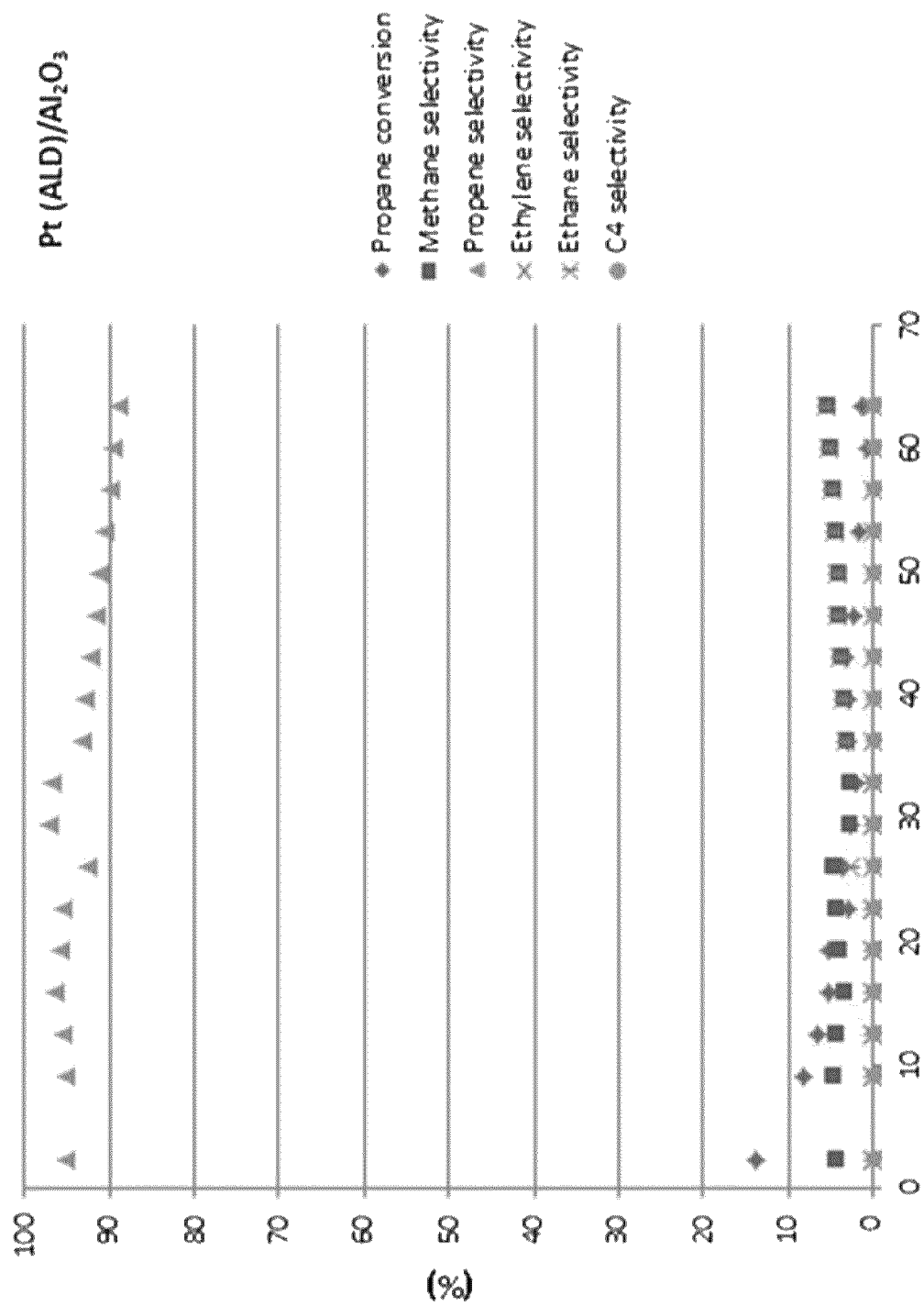
FIG. 18 illustrates conversion and selectivity for Pt(ALD)/$Al_2O_3$.
Figure 19:
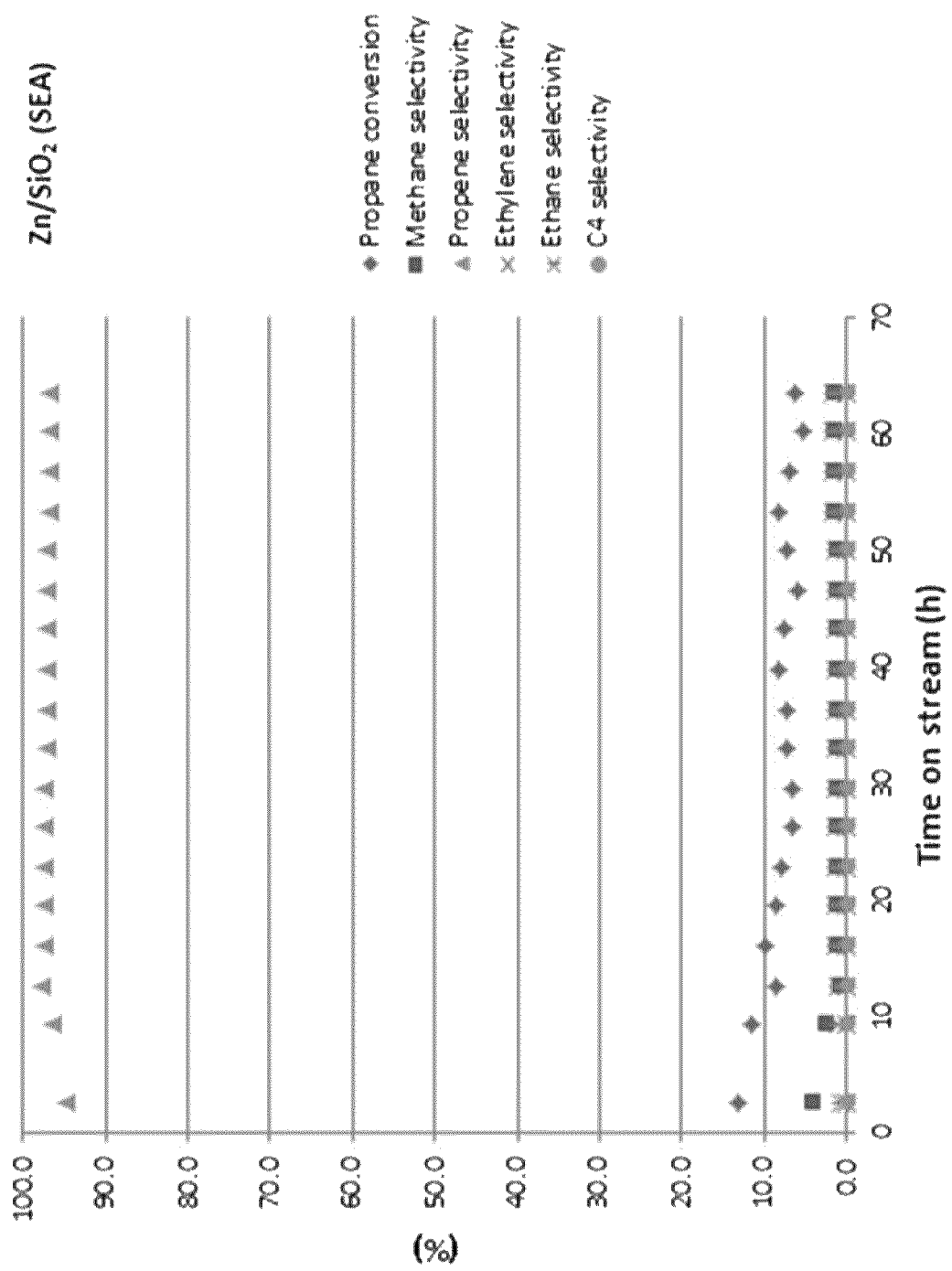
FIG. 19 illustrates conversion and selectivity for a known catalyst Zn/$SiO_2$(SEA).
Figure 20:
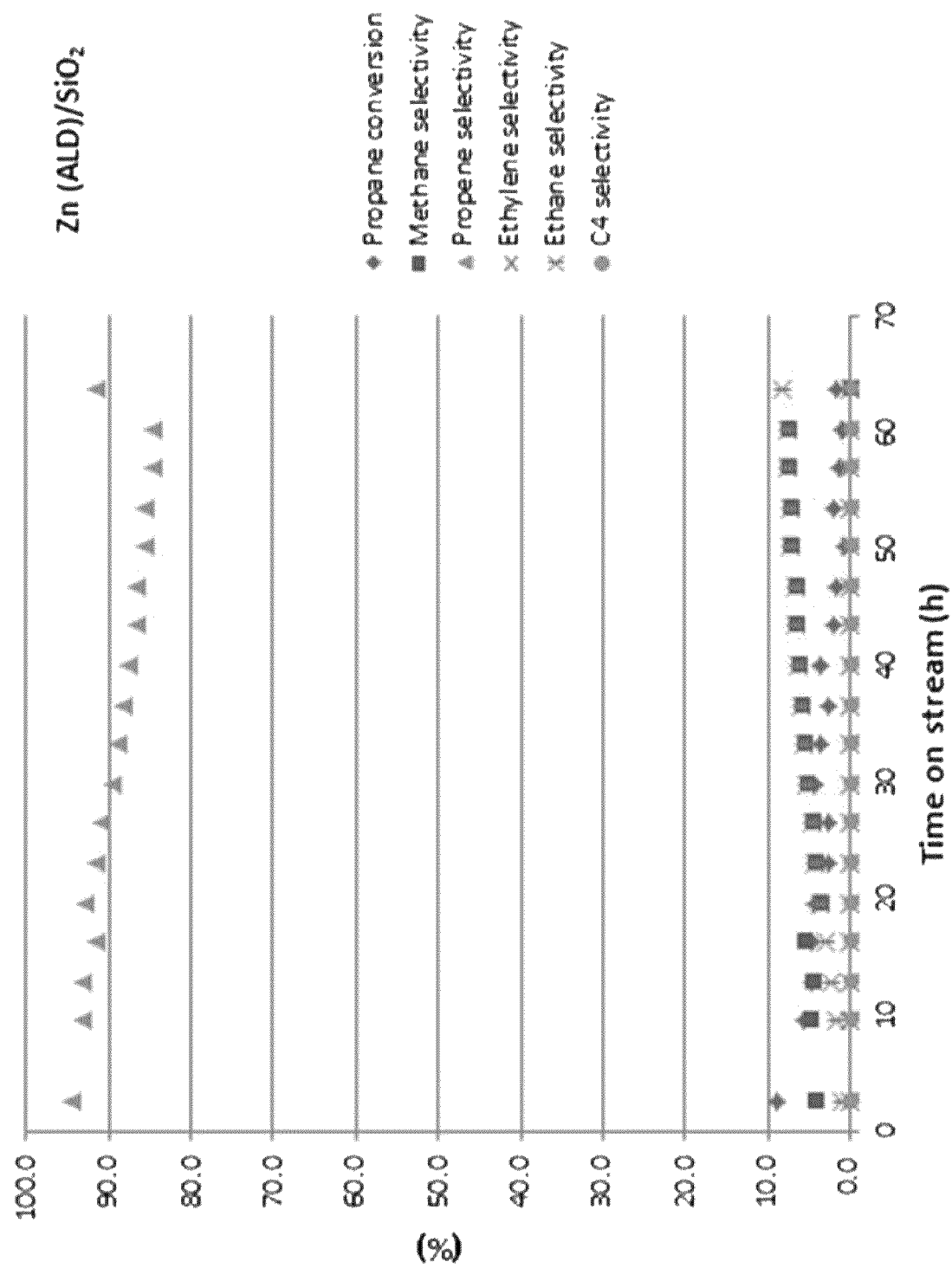
FIG. 20 illustrates conversion and selectivity for Zn(ALD)/$SiO_2$.
Figure 21:
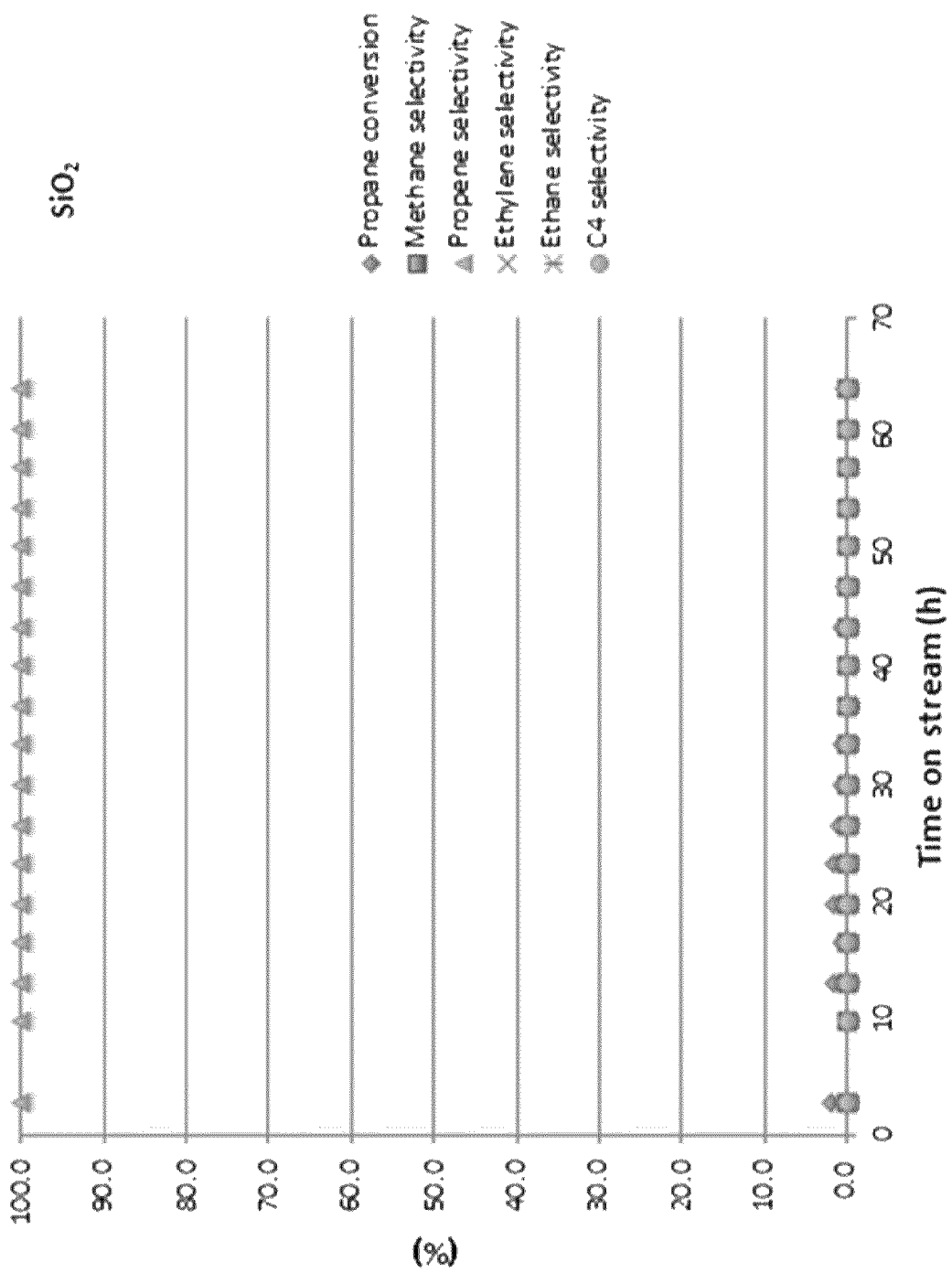
FIG. 21 illustrates conversion and selectivity for $SiO_2$.
Figure 22:
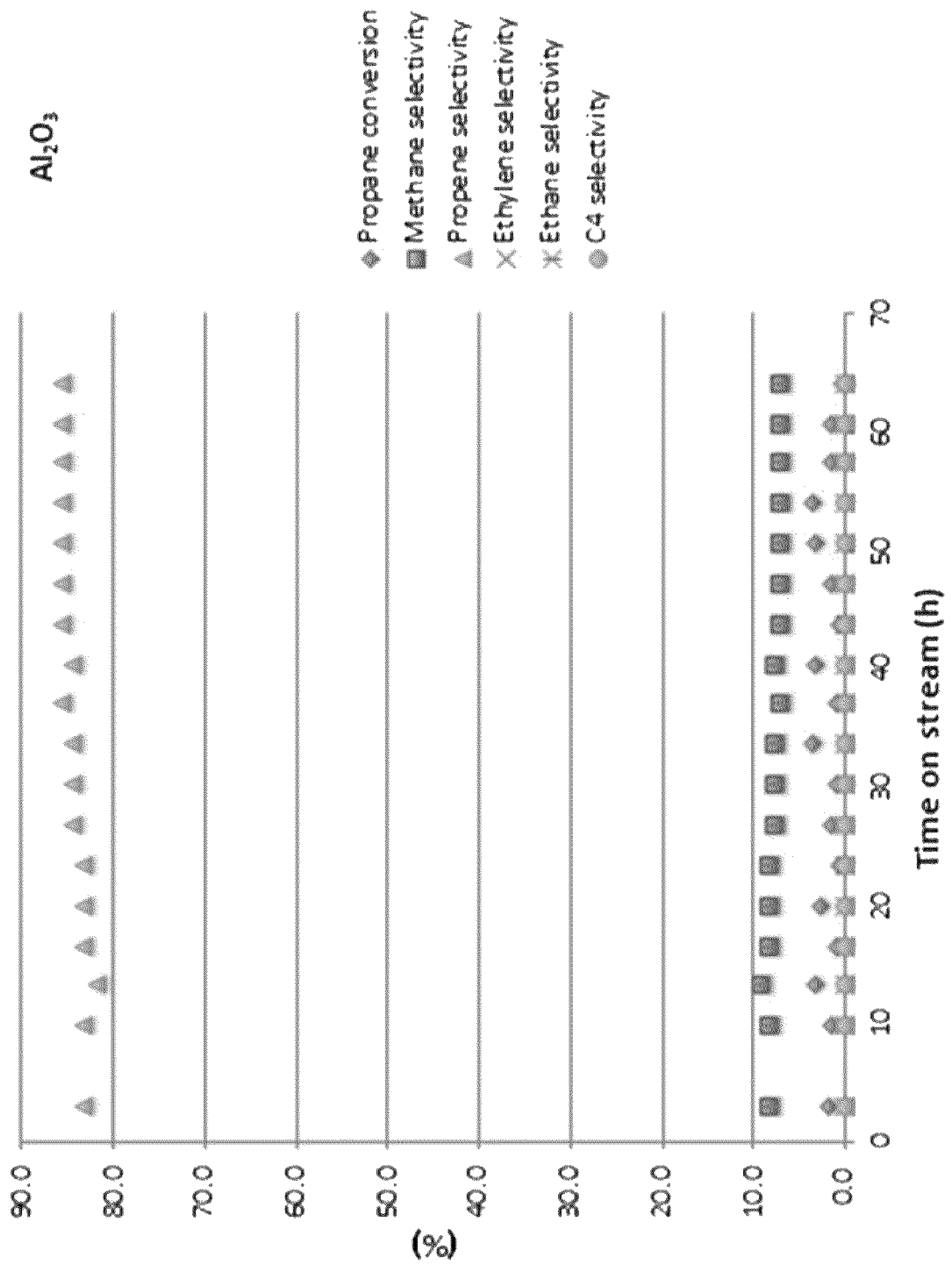
FIG. 22 illustrates conversion and selectivity for $Al_2O_3$.

FIG. 16-18 demonstrate catalysts using prior combination of platinum with alternative substrates to silica. As can be seen, while each does demonstrate selectivity for propene, the conversion rate for propane is very low, below ~10%, when compared with the ~70% observed in FIGS. 8, 12, and 13 for embodiments described herein of Pt/ZnO/SiO2.

Figure 8:
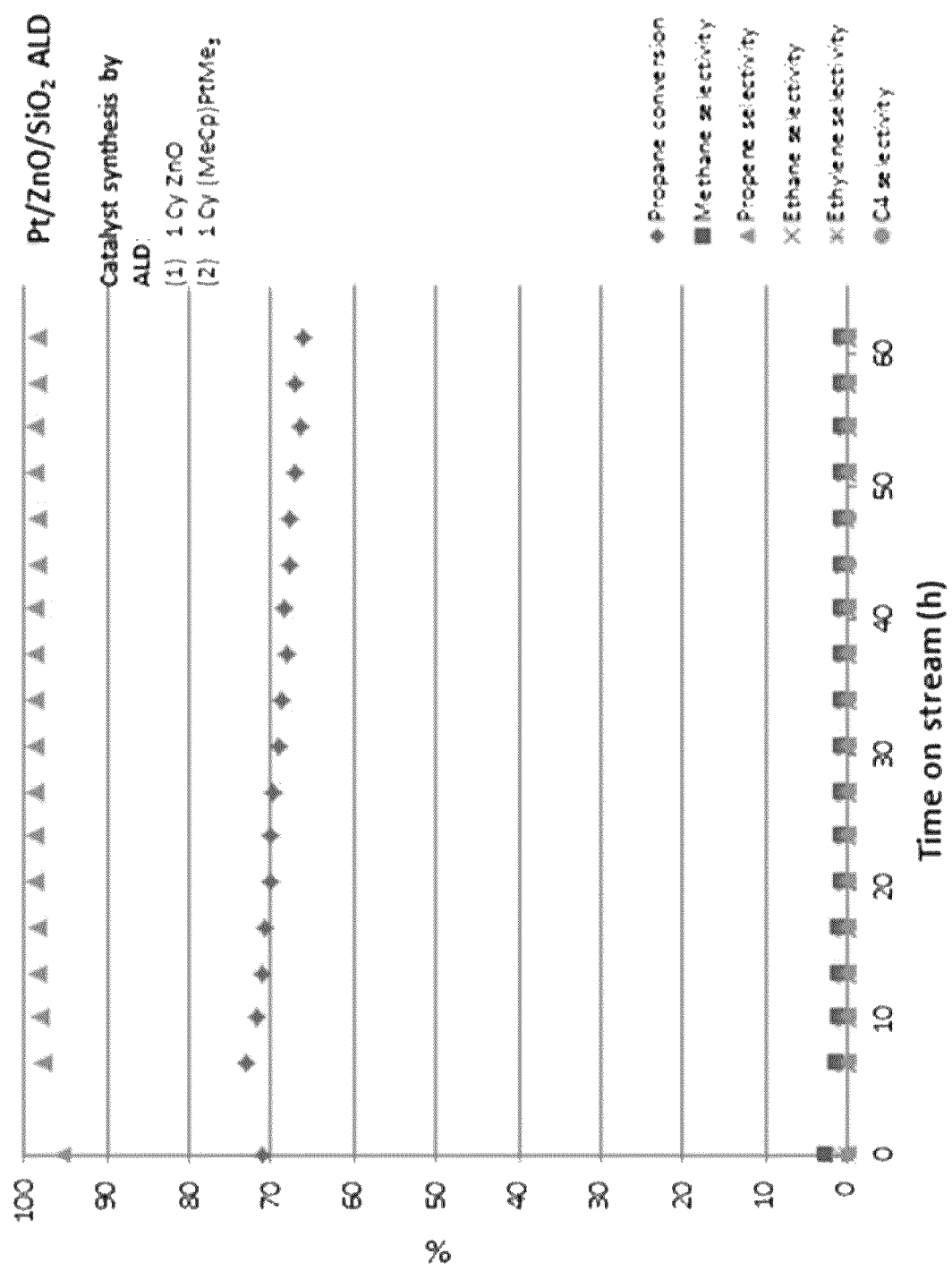
FIG. 8 illustrates conversion and selectivity for Pt/ZnO/$SiO_2$ (ALD) where both Pt and ZnO sites grafted by ALD.
Figure 9:
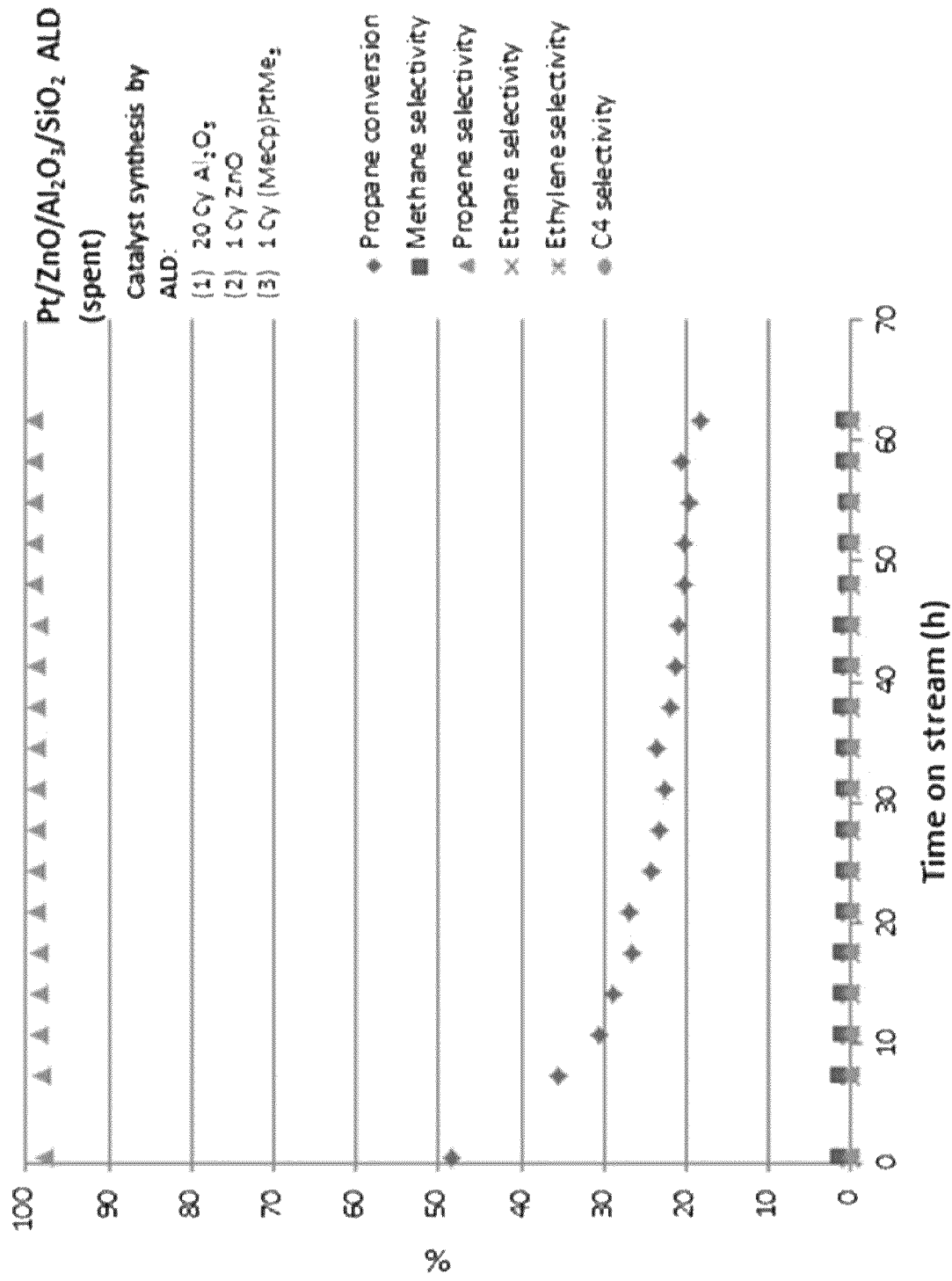
FIG. 9 illustrates conversion and selectivity for the spent Pt/ZnO/$Al_2O_3$/$SiO_2$ (ALD) catalyst.
Figure 11:
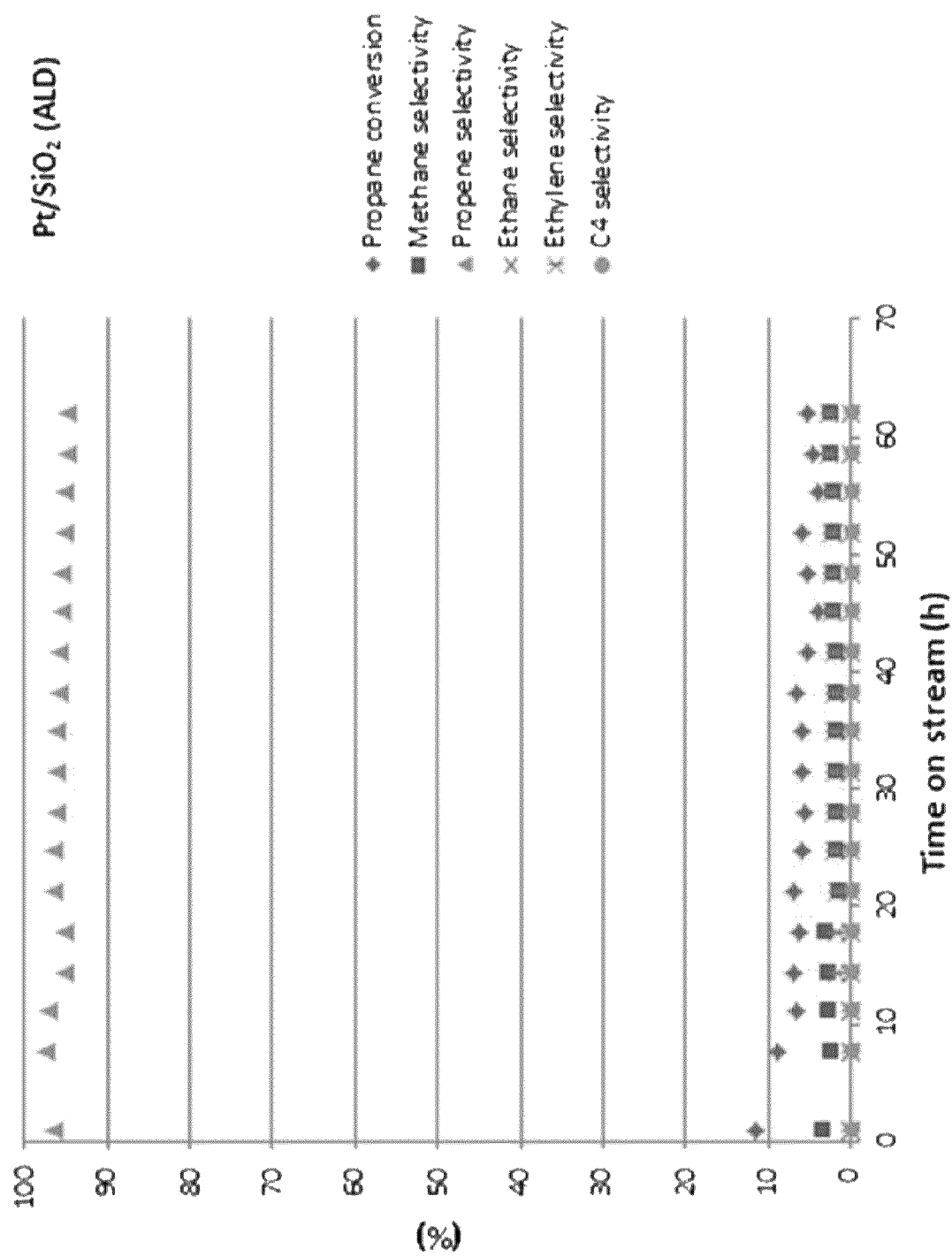
FIG. 11 illustrates conversion and selectivity for Pt/$SiO_2$ (ALD).

A comparison of the conversion rates shown in FIG. 11 for Pt/SiO2 vs FIG. 8 showing Pt/ZnO/SiO2 highlights the surprising and dramatic increase in conversion rate through the addition of zinc oxide. The conversion rate of the embodiment of FIG. 8 is ~70% while the use of a catalyst with platinum directly on silica shows a conversion rate quickly dropping below ~10%.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A catalyst comprising:
    a substrate;
    an intermediate layer having a partial monoatomic thickness or a monoatomic thickness and comprising $MO_x$ wherein $MO_x$ is selected from the transition metal oxides consisting of $TiO_2$, $ZrO_2$, $CoO_x$ (x=1-1.5), $ZnO$, and $MnOx$ (x=1 to 4), the intermediate layer deposited on the substrate; and
    a catalyst layer comprising a platinum group metal, the catalyst layer deposited on the metal oxide intermediate layer;
    wherein the catalyst exhibits at least 95% selectivity for propene and further wherein the catalyst exhibits at least a 70% propane conversion.

2. The catalyst of claim 1, wherein the substrate comprises silica.

3. The catalyst of claim 1, wherein the catalyst layer consists essentially of a platinum material.

4. The catalyst of claim 1 further comprising an overcoat layer deposited on the catalyst.

5. The catalyst of claim 1, wherein the overcoat layer comprises multiple layers of alumina.

6. A catalyst for alkane dehydrogenation comprising:
    a substrate consisting essentially of silica;
    an intermediate layer consisting essentially of ZnO, the intermediate layer deposited on the substrate; and
    a catalyst layer consisting essentially of a platinum group metal, the catalyst layer deposited on the intermediate layer;
    wherein the catalyst exhibits at least 95% selectivity for propene and further wherein the catalyst exhibits at least a 70% propane conversion.

7. The catalyst of claim 6, wherein the catalyst exhibits a turnover frequency of at least 100,000 per hour after 50 hours.

8. The catalyst of claim 6, wherein the intermediate layer has a mono atomic layer thickness.

9. The catalyst of claim 6, wherein the intermediate layer has a partial mono atomic layer thickness.

* * * * *